United States Patent
Okoye

(10) Patent No.: US 12,133,918 B2
(45) Date of Patent: Nov. 5, 2024

(54) PARTIALLY PRE-GELATINIZED CASSAVA STARCH AS PHARMACEUTICAL EXCIPIENT

(71) Applicant: Patrick Chukwuemeka Okoye, Fishkill, NY (US)

(72) Inventor: Patrick Chukwuemeka Okoye, Fishkill, NY (US)

(73) Assignee: Griffin Gamma, LLC, Fishkill, NY (US)

(*) Notice: Subject to any disclaimer, the term of this patent is extended or adjusted under 35 U.S.C. 154(b) by 0 days.

(21) Appl. No.: 17/811,446

(22) Filed: Jul. 8, 2022

(65) Prior Publication Data

US 2023/0106181 A1    Apr. 6, 2023

Related U.S. Application Data

(60) Provisional application No. 63/261,958, filed on Oct. 1, 2021.

(51) Int. Cl.
    *A61K 9/20*     (2006.01)
    *A61K 31/085*   (2006.01)
    *A61K 31/616*   (2006.01)

(52) U.S. Cl.
    CPC .......... *A61K 9/2095* (2013.01); *A61K 9/2059* (2013.01); *A61K 31/085* (2013.01); *A61K 31/616* (2013.01)

(58) Field of Classification Search
    CPC .. A61K 9/2095; A61K 9/2059; A61K 31/085; A61K 31/616; A61K 9/146; A61K 31/09; A61K 47/36
    See application file for complete search history.

(56) References Cited

U.S. PATENT DOCUMENTS

| | | | |
|---|---|---|---|
| 2,098,293 A | 11/1937 | Jefferies | |
| 2,216,179 A | 10/1940 | Bauer | |
| 2,427,328 A | 9/1947 | Schopmeyer | |
| 2,464,081 A | 3/1949 | Hansen | |
| 3,079,283 A | 2/1963 | Dreissen | |
| 3,137,592 A | 6/1964 | Protzman et al. | |
| 3,159,505 A | 12/1964 | Burgess | |
| 3,196,044 A | 7/1965 | Kott et al. | |
| 3,399,081 A | 8/1968 | Bernetti | |
| 3,490,742 A | 1/1970 | Nichols et al. | |
| 3,607,394 A | 9/1971 | Germino et al. | |
| 3,622,677 A | 11/1971 | Short | |
| 4,072,535 A | 2/1978 | Short et al. | |
| 4,369,308 A | 1/1983 | Trubiano | |
| 5,073,380 A | 12/1991 | Babu et al. | |
| 5,164,014 A | 11/1992 | Brancq et al. | |
| 5,462,747 A | 10/1995 | Radebaugh et al. | |
| 6,143,324 A * | 11/2000 | Michaud | C08B 30/12 514/960 |
| 6,303,147 B1 | 10/2001 | Gilis | |
| 7,186,293 B2 * | 3/2007 | Cunningham | C08J 3/122 106/206.1 |
| 8,158,146 B2 | 4/2012 | Kadosh et al. | |
| 8,435,564 B2 | 5/2013 | Eeckman et al. | |
| 9,198,861 B2 | 12/2015 | Park et al. | |
| 9,963,581 B2 | 5/2018 | Ichihara et al. | |
| 10,172,368 B2 | 1/2019 | Hanchett et al. | |
| 10,265,272 B2 | 4/2019 | Politi et al. | |
| 10,888,523 B2 | 1/2021 | Mittal | |
| 2003/0215499 A1 * | 11/2003 | Shi | A61K 9/2059 264/109 |
| 2006/0008521 A1 | 1/2006 | Zhang et al. | |
| 2008/0008751 A1 | 1/2008 | Fox | |
| 2008/0008752 A1 | 1/2008 | Hrakovsky et al. | |
| 2011/0081413 A1 | 4/2011 | Omray | |
| 2011/0165235 A1 | 7/2011 | Paetz et al. | |
| 2015/0216869 A1 * | 8/2015 | Brew | A61K 36/185 514/263.31 |
| 2016/0338395 A1 | 11/2016 | Kawata et al. | |
| 2022/0047511 A1 | 2/2022 | De Miguel et al. | |

FOREIGN PATENT DOCUMENTS

WO   2012003172 A1   1/2012

OTHER PUBLICATIONS

Hasani et al (Hasani et al. 2015, researchgate.net/publication/282217531). (Year: 2015).*
Hartesi et al. (Hartesi et al. 2016, globalresearchonline.net/journalcontents/v41-2/14.pdf) (Year: 2016).*
Morovati (Morovati et al. 2017 ncbi.nlm.nih.gov/pmc/articles/PMC5843298) (Year: 2017).*
Montagnac et al. (Processing Techniques to Reduce Toxicity and Antinutrients of Cassava for Use as a Staple Food, Sep. 16, 2008) (Year: 2008).*
Aspirin monographs. USP. (n.d.). Retrieved Jun. 24, 2022, from https://www.uspnf.com/notices/aspirin-monographs.
USP Monographs: Guaifenesin. (n.d.). Retrieved Jun. 24, 2022, from http://www.pharmacopeia.cn/v29240/usp29nf24s0_m35990.html.

* cited by examiner

*Primary Examiner* — Lezah Roberts
*Assistant Examiner* — Abdulrahman Abbas
(74) *Attorney, Agent, or Firm* — Dunlap Bennett & Ludwig, PLLC; Anna L. Kinney

(57) ABSTRACT

A hybrid composition of partially pre-gelatinized cassava starch powder is herein disclosed. The hybrid composition is obtained by a pre-compaction process and a wet-granulation process, and the partially pre-gelatinized cassava starch including birefringent portions and non-birefringent portions. The hybrid composition is formulated for use in, for example, tablets, and may be used as a multi-functional excipient in various powder formulations.

18 Claims, 11 Drawing Sheets

PARTIALLY PRE-GELATINIZED CASSAVA STARCH AS PHARMACEUTICAL EXCIPIENT

CROSS-REFERENCE TO RELATED APPLICATION

This application claims the benefit of priority of U.S. provisional application No. 63/261,958, filed Oct. 1, 2021, the contents of which are herein incorporated by reference.

FIELD OF THE INVENTION

The present invention relates to a pre-compacted and wet-granulated hybrid composition comprising physically modified, partially pre-gelatinized cassava (*Manihot esculenta*) starch, which is useful as a multi-functional excipient for cosmetic, nutraceutical, and pharmaceutical solid dosage forms, a method of making such composition, and solid dosage forms prepared using the composition.

BACKGROUND OF THE INVENTION

Cassava root and tubers may come in either sweet-type or bitter-type. Bitter-type root and tubers may have higher cyanide levels compared to the sweet-type, either in the form of glycosidic cyanogens, non-glycosidic cyanogens, or free cyanide (such as linamarin and lotaustralin, hydrogen cyanide or other cyanide compounds) that make products produced from it to be unsuitable for human consumption without specific and expensive processing. Thus, manufacture of edible or food grade cassava starch and flour involves methods necessary to reduce the cyanide levels in the cassava product to acceptable levels of such impurities.

Cassava is an important tropical root crop providing staple food to about one billion people globally. The presence of the two cyanogenic glycosides, linamarin and lotaustralin, in cassava is a major factor limiting its use as food or feed. Traditional processing techniques practiced in local, non-mechanized cassava production are known to reduce cyanide in tubers and leaves. Specifically, drying is the most ubiquitous processing operation in many tropical countries. Sun drying eliminates more than 70% of the cyanide compared to oven drying because of the prolonged contact time between linamarin and the glucosides in sun drying. Additionally, soaking followed by boiling is better than soaking or boiling alone in removing cyanide. Traditional African food products such as garri and fufu are made by a series of operations such as grating, dewatering, fermenting, and roasting. During the various stages of garri manufacture, about 80 to 95% cyanide is estimated to be eliminated.

Published patent publications (PCT/US2011/042111; WO2012003172A1) claimed that many common starch production methods are performed on a small, household scale and may not be suitable for use on an industrial scale, for example, due to the use of large quantities of wash water. The cited patent publications also claimed that multiple washes with large amounts of water may impact certain characteristics of the resulting cassava flour, for example, the crude fiber content of the cassava flour and/or the viscosity of the cassava flour. Thus, cyanide removal from cassava is not possible without serious economic and financial considerations. According to the published patent applications (PCT/US2011/042111; WO2012003172A1), enzymatic process is necessary to release cyanide from its glycosides (linamarin and lotaustralin) and/or conversion to acetone cyanohydrin which then spontaneously dissociates to volatile hydrogen cyanide, linamarin and lotaustralin, under the process pH. The cited published patent publications (PCT/US2011/042111; WO2012003172A1) further claimed that the process may comprise providing a mash comprising crushed cassava root, adjusting a pH of the mash, incubating the mash at the appropriate temperature for at least 30 minutes, pressing the mash to remove excess water and provide a cassava cake, and processing the cassava cake to provide a low cyanide cassava flour.

The applicant of the present invention finds that such claims made within patent publications (PCT/US2011/042111; WO2012003172A1) to not represent the only pathway to producing acceptable, detoxified, food-grade cassava flour and/or starch, as herein disclosed. There is need for multi-functional cassava starch excipient which exhibits excellent compression profiles, good disintegration and dissolution properties, aesthetics, excellent stability profile, texture, and good flowability, as herein disclosed. Such cassava starch excipient should be neither chemically modified nor enzymatically treated.

SUMMARY OF THE INVENTION

One embodiment of the present invention is a pre-compacted and wet-granulated hybrid composition comprising physically modified, partially pre-gelatinized cassava (*Manihot esculenta*) starch, that is a free-flowing binder-disintegrant powder material, which is useful as a multi-functional excipient for solid dosage forms, foods and cosmetic powders; a method of making such composition for use in cosmetic, nutriceuticals, and pharmaceutical loose powder products, powder compacts, foods, and solid dosage forms.

Such pre-compacted and wet-granulated hybrid composition is characterized by a predominance of modified particles having both birefringent (intact granules) and non-birefringent portions (partially destroyed granules) with ratio in the range of 10:90 to 90:10 (preferably between 30:70 to 70:30), where such granules are partially pre-gelatinized through either mechanical or thermal stress; with an optical rotational range of −15 to +15 degrees (preferably −7 to +7 degrees) under polarized light; a bulk density of 0.40 to 0.75 g/mL; and a cold water solubility of between 1% and 35% (preferably between 2% to 30%). This free-flowing cassava starch derived from a hybrid of pre-compacted and wet-granulated, having compressibility, Carr's Index (CI) between 15 to 40; and an average particle size greater than 50 microns, with a range of 5 to 300 microns (preferably between 10 to 220 microns); a low cyanogenic glycosidic content (of such elements as linamarin or lotaustralin) with values near or less than 1 ppm; and a moisture content of between 7 and 15% by weight (preferably between 9 to 13%).

The applicant of the present invention recognizes previous works that described partially pre-gelatinized starches that are derived wholly or partially from corn, maize, potato (U.S. Pat. No. 4,072,535; US 2006/0008521A1; U.S. Pat. No. 7,186,293B2 [JP 56-28606]; U.S. Pat. Nos. 3,607,394; 6,143,324; 5,164,014); works that specifically applied combination of native starch and pre-compacted starch; as well as wet-granulated starch (U.S. Pat. No. 7,186,293 B2) from corn, maize and potato; works that focused on cassava flour for non-pharmaceutical uses, bakery, snacks, sauces, crackers, baby foods, pet foods, and other suitable foods (PCT/US2011/042111 (mentioned above); WO2012003172A1 (mentioned above); U.S. Pat. Nos. 9,963,581; 3,079,283);

and works that used fully gelatinized starches from maize, potato, corn, yam and tapioca starch (U.S. Pat. Nos. 2,427, 328; 3,622,677; 2,216,179, U.S. Ser. No. 10/172,368, US20160338395). Furthermore, U.S. Pat. No. 3,399,081 describes a solvent process for preparing pre-gelatinized starch using the gelatinizing effects of liquid ammonia in nonaqueous media, including methanol, ethanol, 1-propanol and other non-aqueous solvents. The stated goal of such chemical treatment was to produce a fully gelatinized starch product useful in textile and paper sizing, ink thickener, adhesives and various food uses. The patent (U.S. Pat. No. 3,399,081) claimed that such completely gelatinized starches would not be useful as binder-disintegrants in direct compression tableting because the resulting tablets do not dissolve effectively, but instead form a gummy mass with a dry center. Swelling power by itself does not determine what starch materials will be useful in tableting. This current invention does not employ the use of chemical treatment for pre-gelatinization.

Additionally, U.S. Pat. No. 3,490,742A described a binder-disintegrant comprising non-granular amylose. In the referenced patent, the material is prepared either by fractionating starch or by dissolving granular high amylose starch in water at an elevated temperature. The patent claimed that the cost of non-granular amylose or fractionated amylose which is then gelatinized would be excessive when compared to the cost of the pre-compacted-starch powder of the subject invention. The resultant compacted material might have differing cold-water swelling properties and contain varying amounts of cold-water soluble material depending primarily upon the particular pressure, temperature, and moisture conditions utilized. Specific techniques espoused by the patent included passing the starting starch through the nip of rotating rolls operating at the same or different speeds, as described in U.S. Pat. Nos. 2,098,293; 2,464,081; and 3,196,044, and working the starch in the course of an extrusion operation as shown in U.S. Pat. Nos. 3,137,592 and 3,159,505.

However, none of these aforementioned works specifically applied partial pre-gelatinization comprising pre-compacted and wet-granulation hybrid to cassava starch for use as pharmaceutical excipient, as herein disclosed.

An embodiment of the present invention provides a freely flowable binder-disintegrant pre-compacted and wet-granulated hybrid composition of cassava starch powder most useful in direct compression tableting. In addition, it is less expensive to manufacture than other direct compression tableting vehicles and allows elimination of the pre-granulation steps required with other tableting materials which do not have the flowability needed in direct compression tableting apparatus. The tablets made using the improved tableting vehicle of this invention are hard, non-friable, and readily disintegrate and dissolve in aqueous medium.

The free flowability and size characteristics of this pre-compacted and wet-granulated hybrid composition of cassava starch powder also have proven to be most useful in blending with an active ingredient as an inert filler material in dry powder-containing gelatin capsules. The ingredients blend uniformly to provide uniform dosage loading of the capsules, and the inert, pre-compacted and wet-granulated hybrid composition of cassava starch powder disintegrates rapidly without interfering with the active ingredient when the capsules are ingested. Tablets made using the subject pre-compacted and wet-granulated hybrid composition of cassava starch as binder-disintegrant in combination with an active ingredient have a hardness index with a range of 25 Newton (N) to 150 Newton, preferably between 40 N and 120 N, a friability weight loss less than 1.0% and the tablets disintegrate effectively in an aqueous medium to release the active ingredient; with final tablet dissolution of no less than 85% in 30 minutes (generally, no less than 80% in 5 minutes; and preferably more than 85% in 3 minutes) in selected aqueous medium; and acceptable drug release for oral dosage forms such as immediate release products, buccal tablets, sublingual tablets, and other orally disintegrating dosage forms.

The pre-compacted and wet-granulated hybrid composition of cassava starch powder of the present Invention has been subjected to physical compaction (with or without thermal application) under low moisture conditions with supplementary thermal energy to obtain a pre-compacted and wet-granulated hybrid composition of cassava starch comprising of birefringent (intact granules) and non-birefringent portions (partially destroyed granules) with ratio in the range of 10:90 to 90:10 (preferably between 30:70 to 70:30), where such granules are partially pre-gelatinized through either mechanical or thermal stress; with an optical rotational range of −15 to +15 degrees (preferably −7 to +7 degrees) under polarized light; a bulk density of 0.40 to 0.75 g/mL; and a cold water solubility of between 1% and 35% (preferably between 2% to 30%). This fairly free-flowing Cassava starch derived from a hybrid of pre-compacted and wet-granulated, having compressibility, Carr's Index (CI) between 15 to 40; and an average particle size greater than 50 microns, with a range of 5 to 300 microns (preferably between 10 to 220 microns); a low cyanogenic glycosidic content (of such elements as linamarin or lotaustralin) with values near or less than 1 ppm; and a moisture content of between 7 and 15% by weight (preferably between 9 to 13%).

The present invention was furthered by subjecting the invention to the criteria of Biopharmaceutics Classification System (BCS), noting the possible effects on certain active pharmaceutical ingredients (APIs) including but not limited to ibuprofen, acetaminophen, tramadol, baclofen, naproxen, guaifenesin, amoxicillin, ciprofloxacin, atorvastatin, celecoxib, carisoprodol, meclizine, folic acid, ascorbic acid, diltiazem, ciprofloxacin, dextromethorphan, aspirin, loratadine, sildenafil, amitriptyline, oxycodone, pyridoxine, methylphenidate, diclofenac, cetirizine, codeine, erythromycin, fentanyl, glucosamine, hydromorphone, amphetamines. Literature and experimental data indicate that Acetylsalicylic acid, USP (ASA) and Guaifenesin, USP (GUA) are highly soluble and highly permeable drugs or medicaments, belonging to Class I of the BCS.

The BCS classification is applied as a basis for setting in vitro dissolution specifications and in vivo/in vitro correlation (IVIVC). The BCS suggests that, for high solubility, high permeability (Class 1) drugs, dissolution of the drug or medicament may be the rate-limiting step for drug absorption, and an IVIVC may be expected. The drug product may be considered rapidly dissolving, if not less than 85% of the labeled amount of the drug substance dissolves within 30 minutes, using US Pharmacopeia (USP) Apparatus I at 100 rpm (or Apparatus II at 50 rpm) in a volume of 900 ml or less in each of the following media: (a) 0.1 N HCl or Simulated Gastric Fluid USP without enzymes; (b) a pH 4.5 buffer; (c) a pH 6.8 buffer or Simulated Intestinal Fluid USP without enzymes; and (d) Purified Water, USP as media. In vitro dissolution tests for immediate release solid oral dosage forms, such as tablets and capsule was applied to the current invention. The dissolution application employed standard method based on modified United States Pharmacopeia (USP) Apparatus II (paddle method).

Specifically, Guaifenesin, chemically known as 3-(2-methoxyphenoxy)-1,2-propanediol, is an expectorant, a drug or medicament which increases respiratory tract fluid secretions and helps to loosen phlegm and bronchial secretions. By reducing the viscosity of secretions, guaifenesin increases the efficiency of a cough reflex and of ciliary action in removing accumulated secretions from trachea and bronchi. Guaifenesin is readily absorbed from the intestinal tract and is rapidly metabolized and excreted in urine. Guaifenesin has a typical plasma half-life of approximately one hour. Based on the rapid metabolism and excretion of guaifenesin, typical immediate release dosage tablets of guaifenesin provide only a short window of therapeutic effectiveness for patients that present signs and symptoms described above.

Specifically, Aspirin also known as acetylsalicylic acid (ASA), is a commonly used drug for the treatment of pain and fever due to various causes. Acetylsalicylic acid has both anti-inflammatory and antipyretic effects, relief of migraines, and reducing the risk of major adverse cardiovascular events. This drug also inhibits platelet aggregation and is used in the prevention of blood clots, stroke, and myocardial infarction (MI).

Preferably, Aspirin (Acetylsalicylic acid) and Guaifenesin belonging to BCS Class I were incorporated into certain powder and tablet formulations.

In one embodiment, the powder formulation was designed to contain Acetylsalicylic acid, USP (ASA) as active pharmaceutical ingredient within the range of 10 to 70 percent, preferably 30 to 60 percent (specifically, 45 to 55 percent). The remaining ingredients in the formulation may consist of microcrystalline cellulose as a diluent, in a range of 10 to 40 percent; a pre-compacted and wet-granulated hybrid composition of cassava starch powder (herein also referred to as Starch 1580GG) as a binder or co-diluent in a range of 10 to 30 percent, preferably 15 to 25 percent (specifically 18 to 22 percent); and magnesium stearate (MgSt) as lubricant in a range of 0.1 to 0.9 percent, preferably at 0.25 to 0.75 percent (specifically at 0.4 to 0.6 percent). The powder blend was directly compressed into tablets containing a range of 40 mg to 280 mg of aspirin, preferably 120 mg to 240 mg of aspirin (specifically 180 mg to 220 mg of aspirin), with a target value of 200 mg.

In another embodiment, a similar powder formulation was designed to contain Acetylsalicylic acid, USP (ASA) as active pharmaceutical ingredient within the range of 10 to 70 percent, preferably 30 to 60 percent (specifically, 45 to 55 percent). The remaining ingredients in the formulation may consist of microcrystalline cellulose as a diluent, in a range of 10 to 40 percent; a partially pre-gelatinized corn starch powder (Starch 1500®, a predicate) as a binder or co-diluent in a range of 10 to 30 percent, preferably 15 to 25 percent (specifically 18 to 22 percent); and magnesium stearate (MgSt) as lubricant in a range of 0.1 to 0.9 percent, preferably at 0.25 to 0.75 percent (specifically at 0.4 to 0.6 percent). The powder blend was directly compressed into tablets containing a range of 40 mg to 280 mg of aspirin, preferably 120 mg to 240 mg of aspirin (specifically 180 mg to 220 mg of aspirin), with a target value of 200 mg.

In furtherance of the present invention, another embodiment of powder formulation was designed to contain Guaifenesin, USP (GUA) as active pharmaceutical ingredient within the range of 10 to 90 percent, preferably 60 to 80 percent (specifically, 65 to 75 percent). The remaining ingredients in the formulation may consist of microcrystalline cellulose (MCC), as a diluent, in a range of 5 to 30 percent; a pre-compacted and wet-granulated hybrid composition of cassava starch powder (Starch 1580GG), as a binder or co-diluent, in a range of 10 to 30 percent, preferably 15 to 25 percent (specifically 18 to 22 percent); and Stearic acid (StaC) as lubricant in a range of 0.1 to 0.9 percent, preferably at 0.25 to 0.75 percent (specifically at 0.4 to 0.6 percent), and colloidal silicon dioxide as a flow agent or glidant, in a range of 0.01 to 0.04 percent, preferably 0.015 to 0.025 percent (specifically 0.018 to 0.022 percent). The composition was partially wet-granulated with subsequent dry mixing and compression. The resulting tablets contain a range of 150 mg to 350 mg of Guaifenesin, preferably 270 mg to 320 mg of Guaifenesin (specifically 280 mg to 300 mg of Guaifenesin), with a target value of 294 mg.

In another embodiment, a similar powder formulation was designed to contain Guaifenesin, USP (GUA) as active pharmaceutical ingredient within the range of 10 to 90 percent, preferably 60 to 80 percent (specifically, 65 to 75 percent). The remaining ingredients in the formulation may consist of microcrystalline cellulose (MCC), as a diluent, in a range of 5 to 30 percent; a partially pre-gelatinized corn starch powder (Starch 1500®, a predicate), as a binder or co-diluent, in a range of 10 to 30 percent, preferably 15 to 25 percent (specifically 18 to 22 percent); and Stearic acid (StaC) as lubricant in a range of 0.1 to 0.9 percent, preferably at 0.25 to 0.75 percent (specifically at 0.4 to 0.6 percent), and colloidal silicon dioxide as a flow agent or glidant, in a range of 0.01 to 0.04 percent, preferably 0.015 to 0.025 percent (specifically 0.018 to 0.022 percent). The composition was partially wet-granulated with subsequent dry mixing and compression. The resulting tablets contain a range of 150 mg to 350 mg of Guaifenesin, preferably 270 mg to 320 mg of Guaifenesin (specifically 280 mg to 300 mg of Guaifenesin), with a target value of 294 mg.

Subsequently, the extent of drug or medicament release for each of Aspirin and Guaifenesin tablet formulation was measured as a function of time and storage conditions (also referred to as drug stability study). Specifically, Aspirin and Guaifenesin drug concentrations were analyzed after 1-month, 2-month, and 3-month time points under target accelerated drug stability conditions of 40 degree Celsius and 75 percent relative humidity, in separate formulations.

DETAILED DESCRIPTION OF THE INVENTION

Figure 1A:
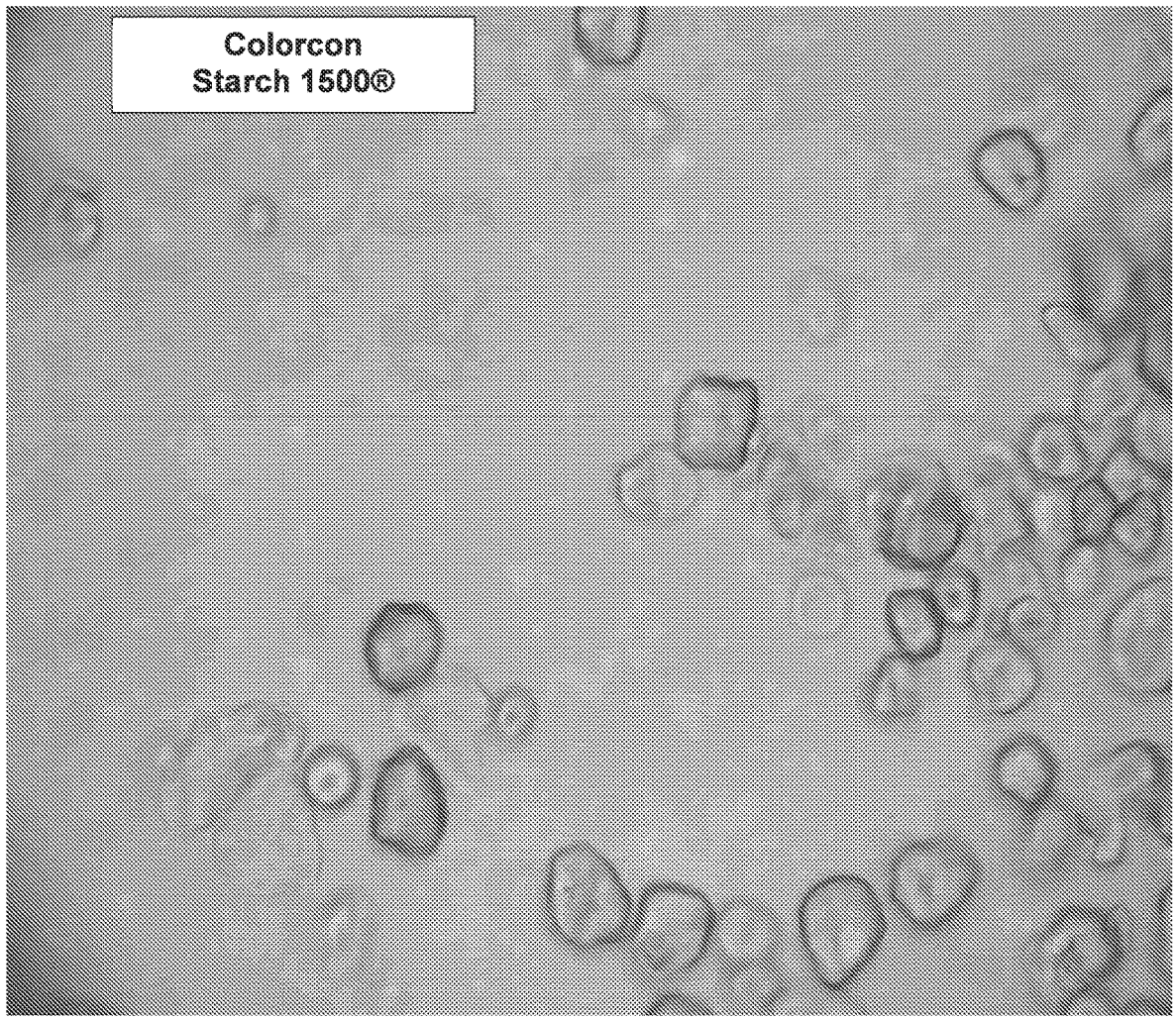
FIGS. 1(a) and 1(b) depict digital microscopy specimens, taken under polarized light, of pre-compacted and wet-granulated hybrid composition of cassava starch (Starch 1580GG, FIG. 1(b)) as compared to Starch 1500® (FIG. 1(a)) at a magnification of 40×.

The following detailed description is of the best currently contemplated modes of carrying out exemplary embodiments of the present invention. The description is not to be taken in a limiting sense but is made merely for the purpose of illustrating the general principles of the present invention, since the scope of the present invention is best defined by the appended claims.

In one embodiment of the present invention, food grade cassava flour and cassava starch are produced using raw cassava tubers as starting material. The raw tubers/roots are collected and washed. The roots are peeled and washed thoroughly in clean water to remove pieces of peel, sand and other dirts. Peeling may be manual or mechanical with clean stainless-steel knives and remove woody tips. The rind is completely removed to ensure low fiber and white color of the finished product. This embodiment includes such techniques to avoid excessive waste of roots during peeling. Further, the roots are crushed properly in clean stainless-steel crusher to obtain uniformly smooth mash. The crushed mash must be uniformly smooth without lumps. In case of non-uniform mash, the material is crushed again until smooth or near smooth mash is obtained. The smoothness of the mash determines the quality, yield, and market value of the finished cassava flour. The mash is loaded into sacks and pressed to remove as much moisture as possible. Pressing is completed when water is no longer dripping from the sacks. Complete dewatering facilitates drying. Pressing should be done immediately after crushing to avoid the onset of fermentation. The pressing time depends on the efficiency of the press and moisture content of the mash. Drying may be conducted using conventional ovens, flash dryers and natural sun drying method. Milling is conducted to obtain fine-textured flour using hammer mill or disc attrition mill.

In another embodiment, the native cassava roots/tubers are placed in a dry sieve. A mechanical device with appropriate grating and blade design is used for cleaning sediment and impurities on raw material. Cleaning efficiencies affect significantly the quality of final starch. Through the collision of raw materials and friction between corner angles of the drum, sand and debris are separated completely. Sewage and sediment are discharged to bottom of the shell through drum gap. Then cleaned raw material is slowly moved to discharging outlet and transported to collector. Further, cleaned cassava tubers and roots are placed into a mechanical rotary or manual sieve for fiber separation. Starch slurry which gets through screen net goes into disc separator for concentration, and fiber enters to fiber pulp dehydrator for further dewatering. Next, the dewatered cassava starch is exposed to further refining process using mechanical hydrocyclone equipment to separate fiber, protein, toxins, impurities, and other contents. The cassava starch slurry is further cleaned and concentrated in this process. Subsequently, the refined cassava starch is dried using a mechanical dryer having the wet starch fed into the feeding inlet through lift under negative pressure. Hot air stream is provided by steam, electrical or gas boiler and wet starch mixes inside and comes out through solid-gas separator, with final cassava starch having moisture content between 7 to 15%.

In another embodiment, the dried cassava starch having moisture content between 7 to 15% is wet-granulated using appropriate granulator possessing either low, medium or high shear blades and such processing is furthered with supplemental compaction using mechanical compactor having single or twin vertical and/or horizontal screw and suitable nip angle and pre-break to produce compacts of durable strength using compaction force ranging from 4 to 25 kN. This present invention shows that:
1. Granulating cassava starch with water or starch paste (range 0.5 to 25% w/w), with or without thermal application, significantly increases the mean particle size more than native cassava starch.
2. Granulating cassava starch with water or starch paste (range 0.5 to 25% w/w), with or without thermal application, shows less birefringence than native starch.
3. Compacting granulated cassava starch using compaction forces in the range of 4 to 25 kN, with or without thermal application, shows far less birefringence than non-compacted, granulated starch and/or native starch.
4. Compaction, with or without thermal application, also increases fractures and potential bonding sites in swollen granules.

In another embodiment, the dried cassava starch having moisture content of about 7-15% is pre-compacted using mechanical compactor having single or twin vertical and/or horizontal screw and suitable nip angle and pre-break to produce compacts of durable strength using compaction force ranging from 4 to 25 kN; and such processing is furthered with supplemental wet-granulation using appropriate granulator having low, medium, or high shear. The present invention shows that:
1. Granulating pre-compacted cassava starch with water or starch paste (range 0.5 to 25% w/w), with or without thermal application, significantly increases the mean particle size more than native cassava starch.
2. Granulating pre-compacted cassava starch with water or starch paste (range 0.5 to 25% w/w), with or without thermal application, shows less birefringence than native starch.
3. Pre-compacting cassava starch using compaction forces in the range of 4 to 25 kN, with or without thermal application, shows far less birefringence than non-compacted, granulated starch and/or native starch.
4. Pre-compacting, with or without thermal application, also increases fractures and potential bonding sites in swollen granules.

Making reference to the FIGURES, the present invention references U.S. Pat. No. 4,072,535 (Starch 1500® based on pre-compacted, partially pre-gelatinized corn starch) for exemplary, comparative review, as well as a predicate.

Figure 1B:
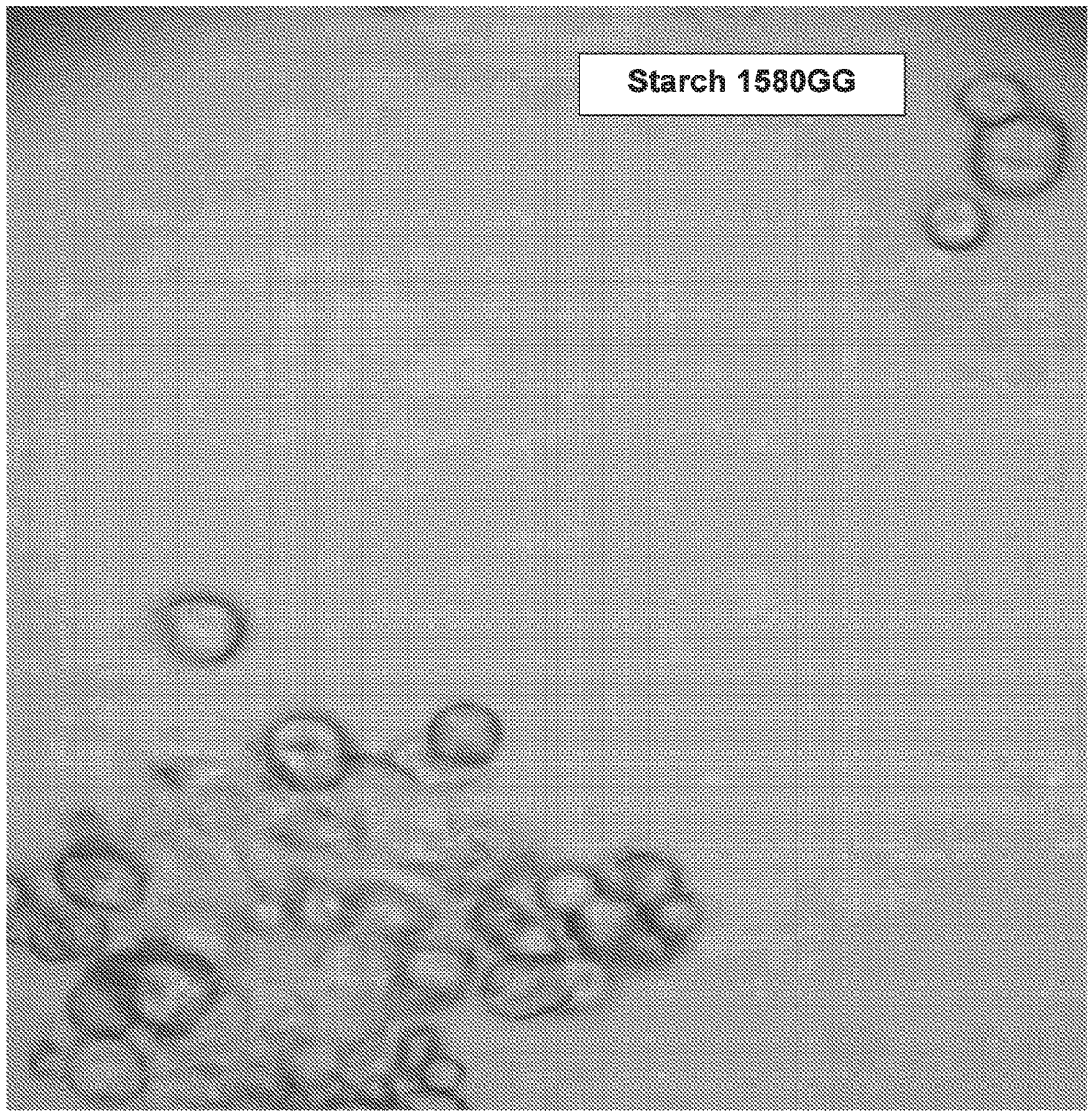

FIGS. 1(a) and 1(b) depict digital microscopy specimens, taken under polarized light, of pre-compacted (Starch 1580GG) as compared to Starch 1500® at a magnification of 40×.

Figure 2A:
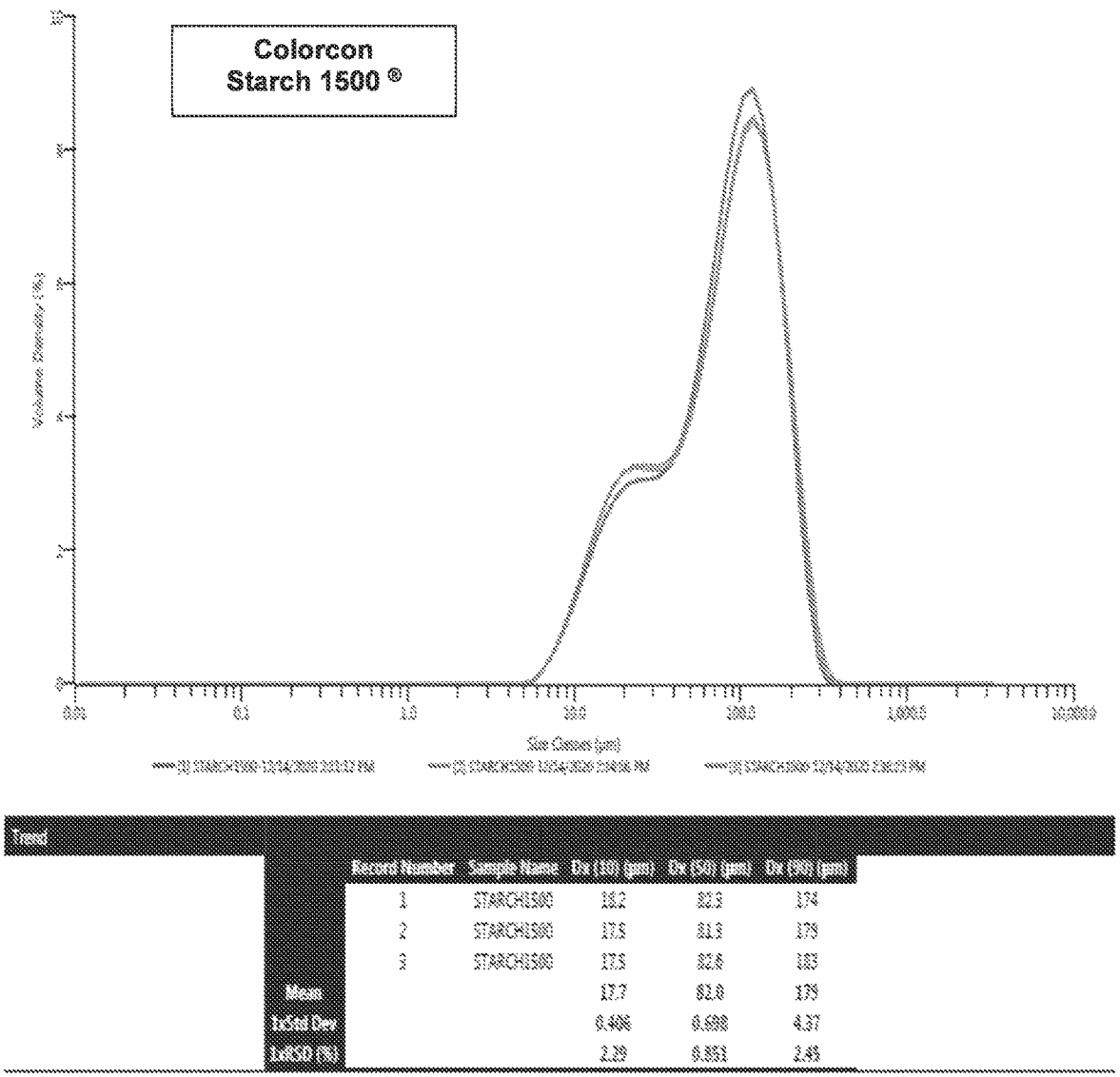
FIGS. 2(a) and (2b) depict a particle size analysis for pre-compacted and wet-granulated hybrid composition of cassava starch (Starch 1580GG) as compared to Starch 1500® useful in accordance with the present invention (Malvern laser diffraction Instrument was employed for this analysis).
Figure 2B:
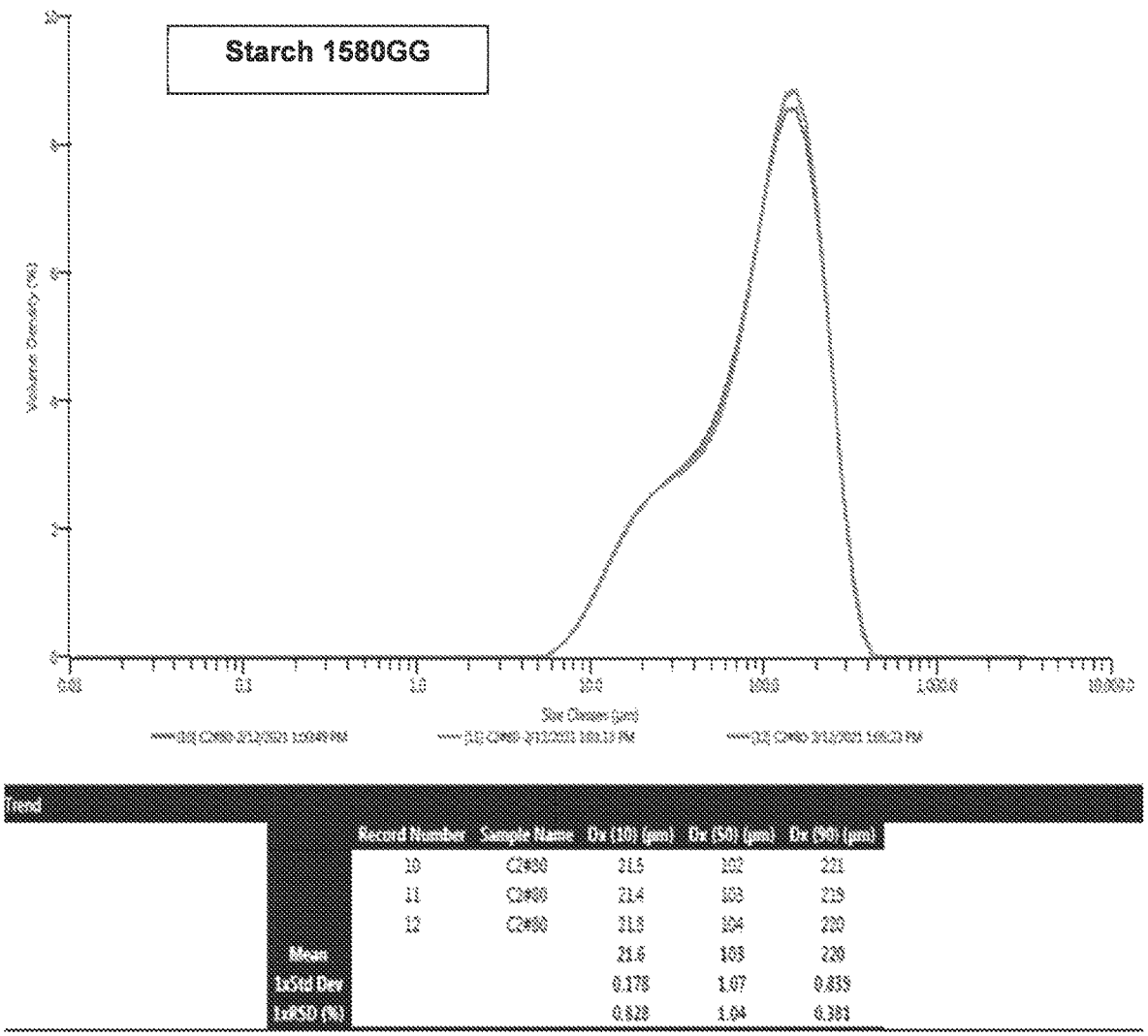

FIGS. 2(a) and 2(b) depict a particle size analysis for pre-compacted and wet-granulated hybrid composition of cassava starch (Starch 1580GG) as compared to Starch 1500® useful in accordance with the present invention (Malvern laser diffraction Instrument was employed for this analysis).

As shown below, Table 1 depicts the formulation design using Guaifenesin, USP (GUA) as active pharmaceutical ingredient. The pre-compacted and wet-granulated hybrid composition of cassava starch (Starch 1580GG) was compared to Starch 1500® as a binder/disintegrant in the formulation.

TABLE 1

Preparation of Guaifenesin Tablet Blend

| Phase | Amount/tablet (% w/w) | Function |
|---|---|---|
| A. Wet granulation | | |
| Guaifenesin, USP | 70.00 | Active Ingredient |
| Starch 1580 GG (or Starch 1500 as predicate) | 16.00 | Binder |
| B. Dry mixing | | |
| Microcrystalline cellulose | 9.48 | Diluent |
| Starch 1580 GG (or Starch 1500 ® as predicate) | 4.00 | Disintegrant |
| Stearic acid | 0.50 | Lubricant |
| Colloidal silicon dioxide | 0.02 | Glidant/Flow agent |
| % Total | 100.00 | |

As shown below, Table 2 depicts the compression parameters for Guaifenesin tablets. The pre-compacted and wet-granulated hybrid composition of cassava starch (Starch 1580GG) was compared to Starch 1500® as a binder/disintegrant in the formulation.

TABLE 2

Compression Parameters for Guaifenesin Tablets

| Binder (Starch) Type | STARCH 1500 ® | STARCH 1580GG |
|---|---|---|
| Upper Compression Force (KN) | 17 | 17 |
| Ejection force (N) | 100 | 106 |
| Avg. Weight of Tablets (mg) | 439.78 | 428.64 |
| Avg. Hardness (N) | 152.6 | 111.83 |
| Friability (%) | 0.25 | 0.44 |
| Avg. Disintegration time (Sec) | <100 | <60 |

Figure 3:
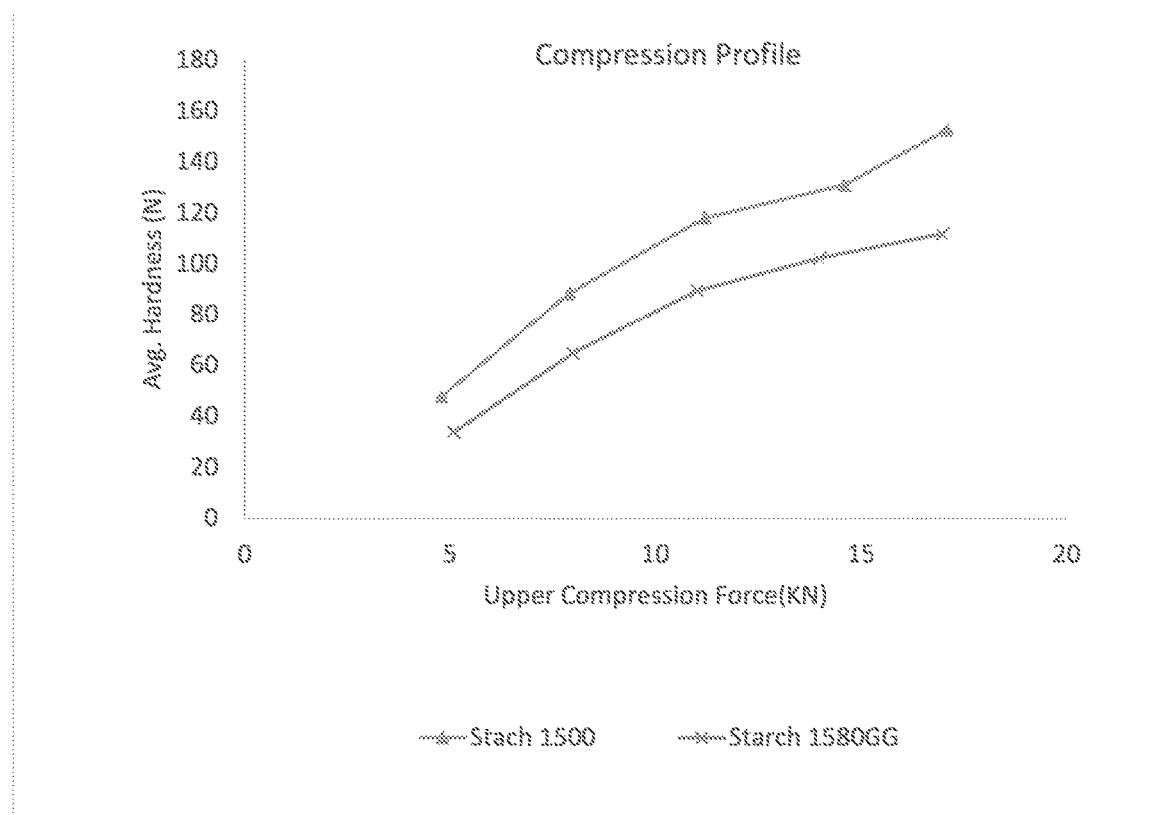
FIG. 3 depicts the Average Tablet Hardness (Compression profile) of Guaifenesin tablets prepared according to the formulation based on using Starch 1580GG (as a binder/disintegrant), as compared to Starch 1500®. Tablet compression was performed using Picola D-8 Rotary Tablet press.

FIG. 3 depicts the Average Tablet Hardness (Compression profile) of Guaifenesin tablets prepared according to the formulation based on using Starch 1580GG (as a binder/disintegrant), as compared to Starch 1500®. Tablet compression was performed using Picola D-8 Rotary Tablet press.

Figure 4:
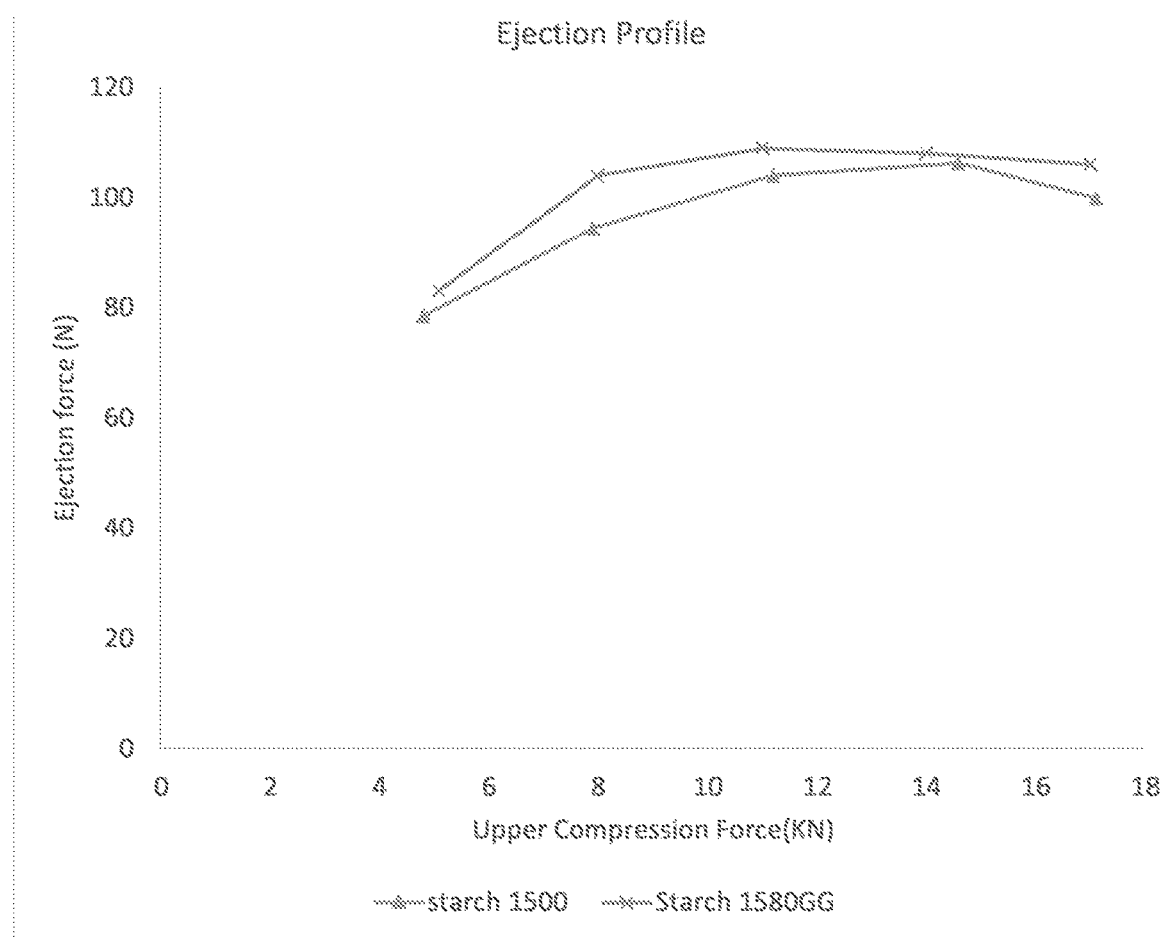
FIG. 4 depicts the Tablet ejection profile of Guaifenesin tablets prepared according to the formulation based on using Starch 1580GG (as a binder/disintegrant), as compared to Starch 1500®. Tablet compression was performed using Picola D-8 Rotary Tablet press.

FIG. 4 depicts the Tablet ejection profile of Guaifenesin tablets prepared according to the formulation based on using Starch 1580GG (as a binder/disintegrant), as compared to Starch 1500®. Tablet compression was performed using Picola D-8 Rotary Tablet press.

Figure 5:
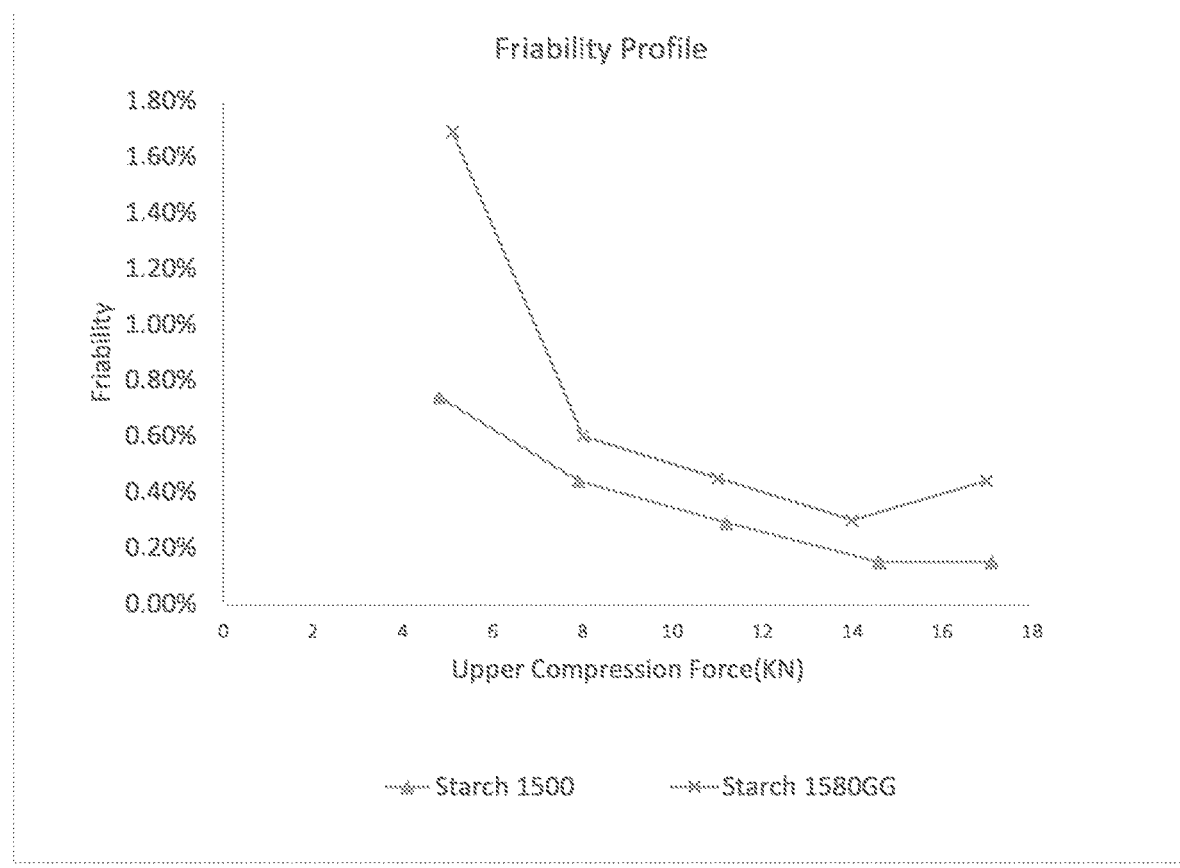
FIG. 5 depicts a friability profile of Guaifenesin tablets prepared according to the formulation based on using Starch 1580GG (as a binder/disintegrant), as compared to Starch 1500®. Tablet friability test was performed using Pharma Test PT Dual Drum Tablet Friabilator.

FIG. 5 depicts a friability profile of Guaifenesin tablets prepared according to the formulation based on using Starch 1580GG (as a binder/disintegrant), as compared to Starch 1500®. Tablet friability test was performed using Pharma Test PT Dual Drum Tablet Friabilator.

Figure 6:
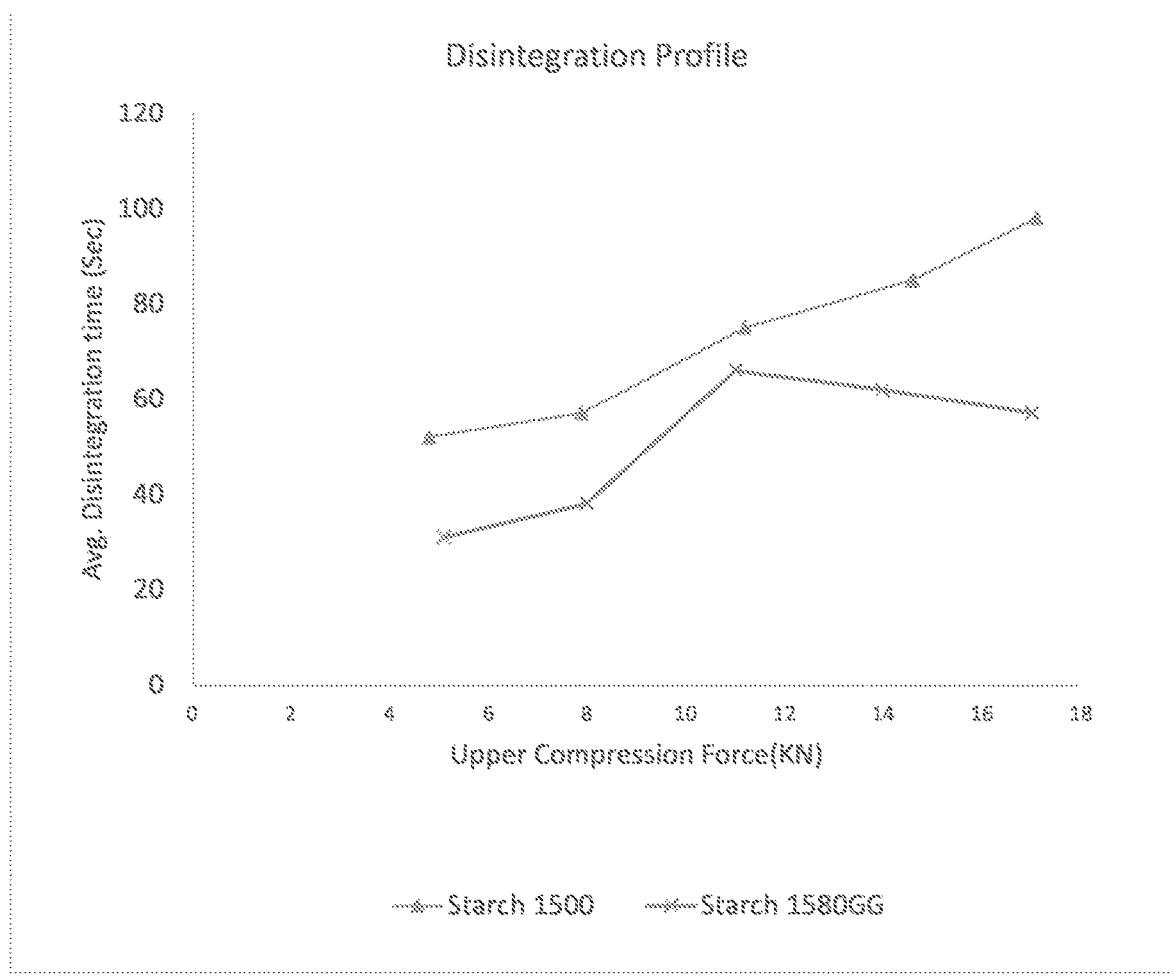
FIG. 6 depicts a disintegration profile of Guaifenesin tablets prepared according to the formulation based on using Starch 1580GG (as a binder/disintegrant), as compared to Starch 1500®. Disintegration was performed using Pharma Test Disintegration Tester PT ZAUTO2.

FIG. 6 depicts a disintegration profile of Guaifenesin tablets prepared according to the formulation based on using Starch 1580GG (as a binder/disintegrant), as compared to Starch 1500®. Disintegration was performed using Pharma Test Disintegration Tester PT ZAUTO2.

Figure 7:
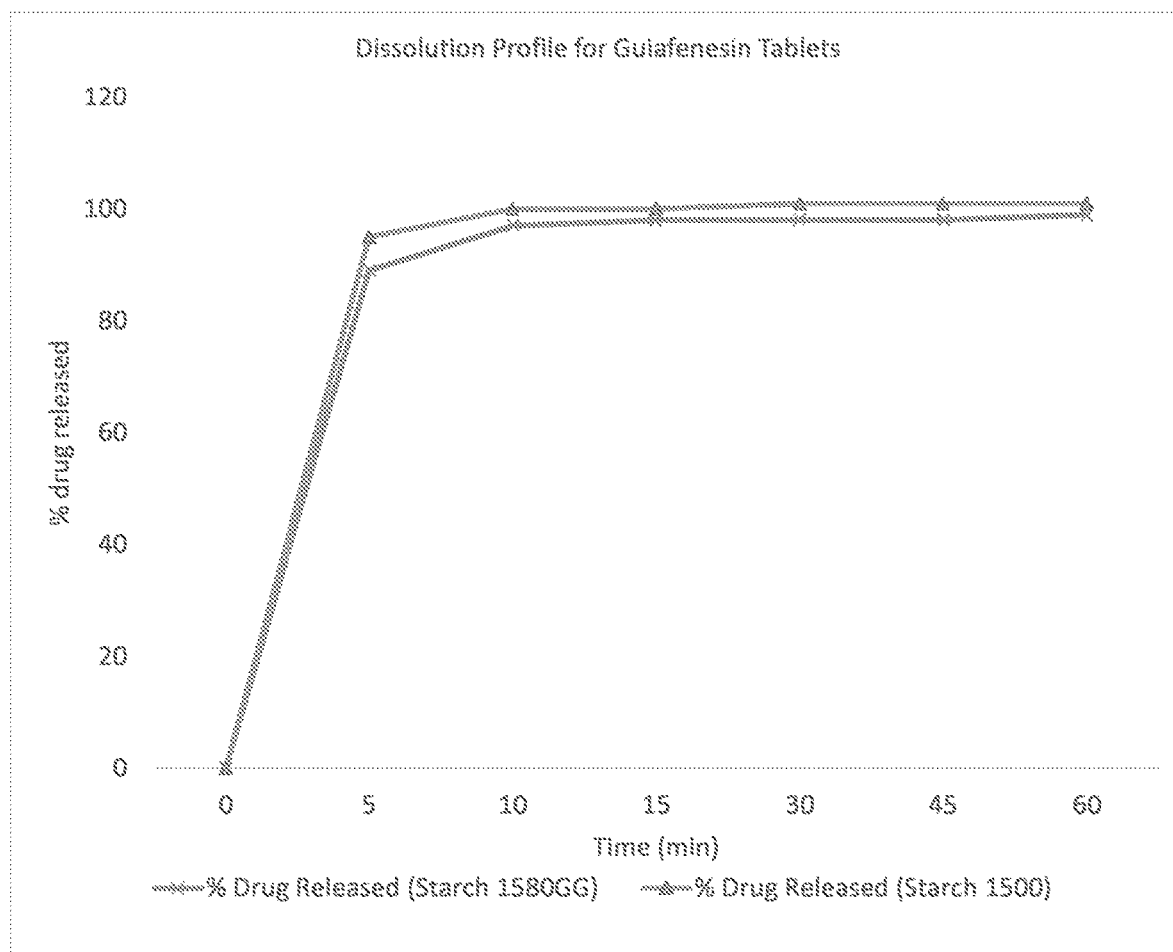
FIG. 7 depicts a dissolution profile of Guaifenesin tablets prepared according to the formulation based on using Starch 1580GG (as a binder/disintegrant), as compared to Starch 1500®. Dissolution was performed using Purified Water, USP and Distek Evolution 6100 Dissolution System.

FIG. 7 depicts a dissolution profile of Guaifenesin tablets prepared according to the formulation based on using Starch 1580GG (as a binder/disintegrant), as compared to Starch 1500®. Dissolution was performed using Purified Water, USP and Distek Evolution 6100 Dissolution System.

As shown below, Table 3 depicts the formulation design using Acetylsalicylic acid, USP (ASA) as active pharmaceutical ingredient. The pre-compacted and wet-granulated hybrid composition of cassava starch (Starch 1580GG) was compared to Starch 1500® as a binder in the formulation.

TABLE 3

Preparation of Aspirin (Acetylsalicylic acid) Tablet Blend

| Phase | Amount/tablet (% w/w) | Function |
|---|---|---|
| Direct Compression Blend | | |
| Acetylsalicylic acid, USP | 50.00 | Active Ingredient |
| Microcrystalline cellulose | 29.50 | Diluent |
| Starch 1580 GG (or Starch 1500® as predicate) | 20.00 | Binder |
| Magnesium stearate | 0.50 | Lubricant |
| % Total | 100.00 | |

As shown below, Table 4 depicts the direct compression parameters for Acetylsalicylic acid (Aspirin) tablets. The pre-compacted and wet-granulated hybrid composition of cassava starch (Starch 1580GG) was compared to Starch 1500® as a binder in the formulation.

TABLE 4

Compression Parameters for Acetylsalicylic acid (Aspirin) Tablets

| Binder (Starch) Type | STARCH 1500 ® | STARCH 1580GG |
|---|---|---|
| Upper Compression Force (KN) | 17 | 17 |
| Ejection force (N) | N/A | N/A |
| Avg. Weight of Tablets (mg) | 396 | 401 |
| Avg. Hardness (N) | 75.2 | 73.4 |
| Friability (%) | 0.44 | 0.59 |
| Avg. Disintegration time (Sec) | <60 | <60 |

As shown below, Table 5 depicts the Drug Stability Study Report for Guaifenesin Tablets at accelerated condition. The tablets were produced using pre-compacted and wet-granulated hybrid composition of Cassava starch (Starch 1580GG) a binder/disintegrant in the formulation.

TABLE 5

Drug Stability Study Report: Guaifenesin Tablets

| | Starch Type | | | |
| --- | --- | --- | --- | --- |
| | 1580GG | | Cassava | |
| | Conditions: | | | |
| | 40 Deg. C. | | 75% RH | |
| | Initial | 1 month | 2 month | 3 month |
| Appearance (Smooth/White) | No Change | No Change | No Change | No Change |
| Weight gain/loss | No Change | No Change | No Change | No Change |
| % Assay (Limit: 63-77%; Target = 70%) | 70.67 | 68.68 | 68.50 | 68.30 |

As shown below, Table 6 depicts the Drug Stability Study Report for Guaifenesin Tablets at accelerated condition. The tablets were produced using Corn starch (Starch 1500®) a binder in the formulation.

TABLE 6

Drug Stability Study Report: Guaifenesin Tablets

| | Starch Type | | | |
| --- | --- | --- | --- | --- |
| | 1500® | | Corn | |
| | Conditions: | | | |
| | 40 Deg. C. | | 75% RH | |
| | Initial | 1 month | 2 month | 3 month |
| Appearance (Smooth/White) | No Change | No Change | No Change | No Change |
| Weight gain/loss | No Change | No Change | No Change | No Change |
| % Assay (Limit: 63-77%; Target = 70%) | 69.00 | 69.46 | 68.82 | 69.25 |

As shown below, Table 7 depicts the Drug Stability Study Report for Acetylsalicylic acid Tablets at an accelerated condition. The tablets were produced using pre-compacted and wet-granulated hybrid composition of Cassava starch (Starch 1580GG) a binder in the formulation.

TABLE 7

Drug Stability Study Report: Acetylsalicylic acid (Aspirin) Tablets

| | Starch Type | | | |
| --- | --- | --- | --- | --- |
| | 1580GG | | Cassava | |
| | Conditions: | | | |
| | 40 Deg. C. | | 75% RH | |
| | Initial | 1 month | 2 month | 3 month |
| Appearance (Smooth/White) | No Change | No Change | No Change | No Change |
| Weight gain/loss | No Change | No Change | No Change | No Change |
| % Assay (Limit: 45-55%; Target = 50%) | 54.03 | 47.26 | 48.23 | 49.75 |

As shown below, Table 8 depicts the Drug Stability Study Report for Acetylsalicylic acid Tablets at an accelerated condition. The tablets were produced using Corn starch (Starch 1500®) a binder in the formulation.

TABLE 8

Drug Stability Study Report: Acetylsalicylic acid (Aspirin) Tablets

| | Starch Type | | | |
| --- | --- | --- | --- | --- |
| | 1500® | | Corn | |
| | Conditions: | | | |
| | 40 Deg. C. | | 75% RH | |
| | Initial | 1 month | 2 month | 3 month |
| Appearance (Smooth/White) | No Change | No Change | No Change | No Change |
| Weight gain/loss | No Change | No Change | No Change | No Change |
| % Assay (Limit: 45-55%; Target = 50%) | 51.89 | 49.85 | 47.01 | 51.99 |

Figure 8:
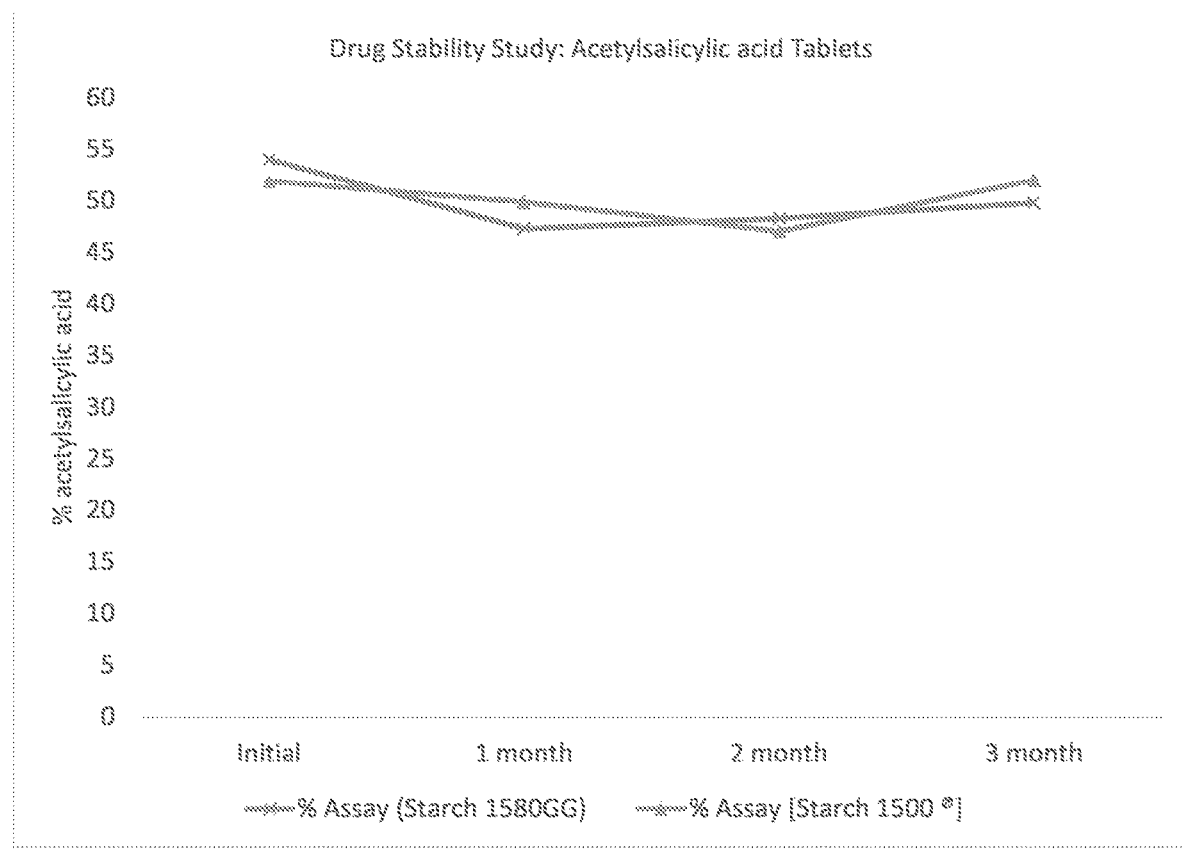
FIG. 8 depicts accelerated drug stability profiles for Acetylsalicylic acid Tablets using (a) Starch 1580GG; and (b) Starch 1500®.

FIG. 8 depicts accelerated drug stability profiles for Acetylsalicylic Acid Tablets using Starch 1580GG; and Starch 1500®. The results demonstrated that Acetylsalicylic Acid product formulated with either Starch 1580GG or Starch 1500® could provide similar presumptive shelf-life.

Figure 9:
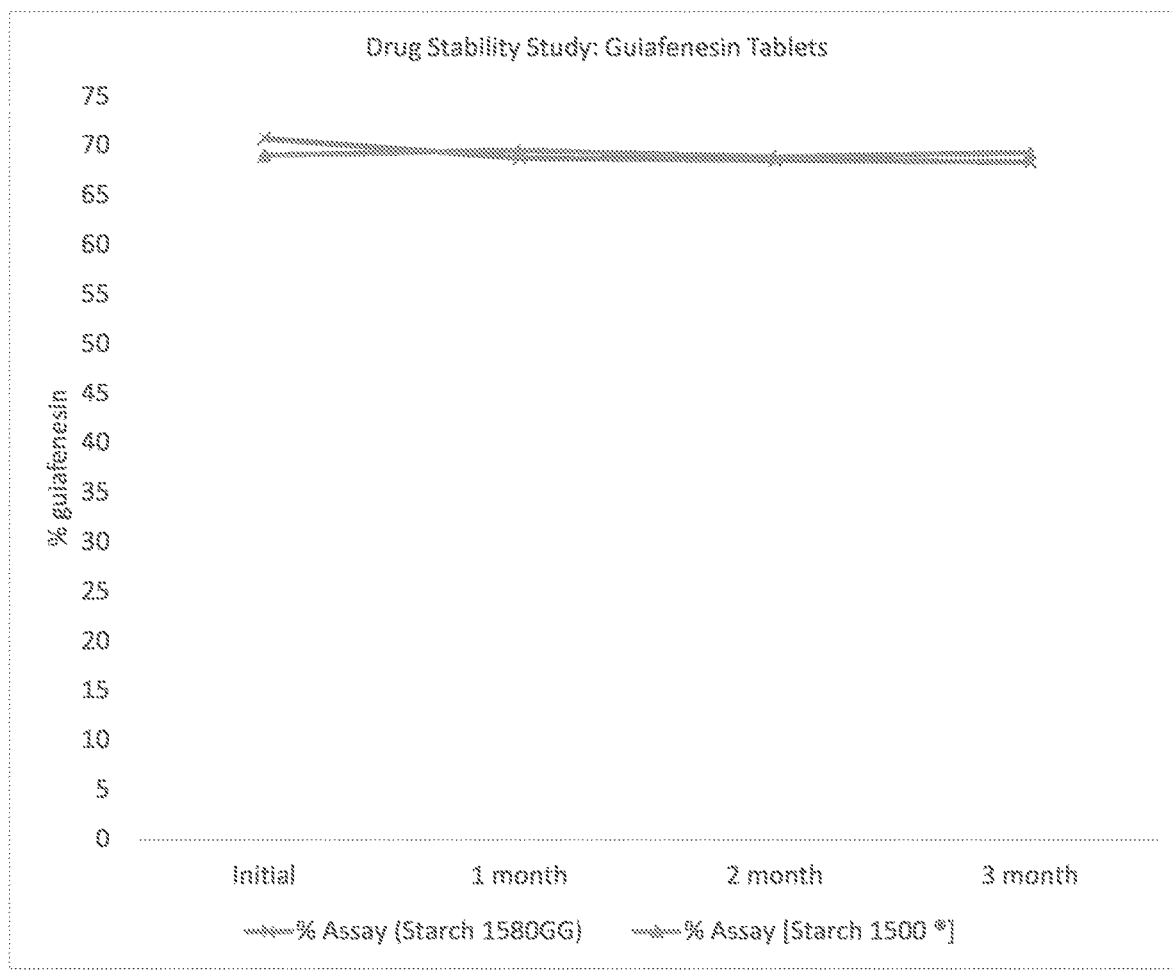
FIG. 9 depicts accelerated drug stability profiles for Guaifenesin Tablets using (a) Starch 1580GG; and (b) Starch 1500®.

FIG. 9 depicts accelerated drug stability profiles for Guaifenesin Tablets using Starch 1580GG: and Starch 1500®. The results demonstrated that Guaifenesin product formulated with either Starch 1580GG or Starch 1500® could provide similar presumptive shelf-life.

The present invention has been described in terms of exemplary embodiments solely for the purpose of illustration. Persons skilled in the art will recognize from this description that the invention is not limited to the embodiments described but may be practiced with modifications and alterations limited only by the spirit and scope of the claims to the present invention.

What is claimed is:

1. A composition of partially pre-gelatinized cassava starch powder, comprising particles obtained by a process including both pre-compaction and wet-granulation, wherein the particles comprise birefringent portions and non-birefringent portions; wherein the particles have a cyanogenic glycosidic content of about 1 part per million or less; and wherein the partially pre-gelatinized cassava starch powder is characterized by a Carr's index between 15 and 35.

2. The composition of claim 1, wherein a ratio of the birefringent portions to the non-birefringent portions is in the range of 10:90 to 90:10.

3. The composition of claim 1, wherein the optical rotational range of the particles is between −15 degrees and +15 degrees under polarized light.

4. The composition of claim 1, wherein the bulk density is between 0.4 grams per milliliter and 0.75 grams per milliliter.

5. The composition of claim 1, wherein the cold water solubility is between 1 percent and 35 percent.

6. The composition of claim 1, wherein the particles have a particle size range of 5 to 300 microns and an average particle size greater than 50 microns.

7. The composition of claim 1, wherein the moisture content is between 7% and 15%.

8. The composition of claim 1, formulated for oral ingestion in a tablet, a capsule, a pressed compact or loose powder.

9. The composition of claim 1, formulated in a cosmeceutical or industrial pressed compact or loose powder.

10. A powder formulation comprising:
the composition of claim 1; and
acetylsalicylic acid.

11. The powder formulation of claim 10, wherein the composition is present in the amount of 5 percent weight to 75 percent weight.

12. A powder formulation comprising:
the composition of claim 1; and
guaifenesin.

13. The powder formulation of claim 12, wherein the composition is present in the amount of 5 percent weight to 75 percent weight.

14. A method of producing the composition of claim 1, comprising:
   providing a cassava starch having a moisture content between 7 to 15%;
   granulating the cassava starch with 0.5 to 25% w/w water or starch paste in a granulator; and
   compacting the cassava starch in a mechanical compactor using a compaction force of from 4 to 25 kN.

15. The method of claim 14, wherein the compacting step occurs before the granulating step.

16. The method of claim 14, wherein the cassava starch is heated during the granulating step.

17. The method of claim 14, wherein the cassava starch is heated during the compacting step.

18. The composition of claim 1, wherein the partially pre-gelatinized cassava starch powder consists of the particles obtained by the process including both pre-compaction and wet-granulation.

* * * * *